US006459080B1

(12) United States Patent
Yin et al.

(10) Patent No.: US 6,459,080 B1
(45) Date of Patent: Oct. 1, 2002

(54) MINIATURIZED DEVICE FOR SEPARATING THE CONSTITUENTS OF A SAMPLE AND DELIVERING THE CONSTITUENTS OF THE SEPARATED SAMPLE TO A MASS SPECTROMETER

(75) Inventors: Hongfeng Yin, San Jose; Sally A Swedberg, Palo Alto; John A Chakel, San Mateo, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/324,344

(22) Filed: Jun. 2, 1999

Related U.S. Application Data

(60) Provisional application No. 60/089,033, filed on Jun. 12, 1998.

(51) Int. Cl.$^7$ .......................... H01J 49/00; B01D 59/44; B01D 15/08; B32B 31/00
(52) U.S. Cl. ...................... 250/288; 250/281; 250/282; 156/272.8; 156/290; 156/292; 210/198.2
(58) Field of Search ...................... 210/198.2; 324/321; 250/288, 281, 282; 156/272.8, 290, 292; 422/70

(56) References Cited

U.S. PATENT DOCUMENTS

| | | | |
|---|---|---|---|
| 4,891,120 A | 1/1990 | Sethi et al. | 204/299 R |
| 4,908,112 A | 3/1990 | Pace | 204/299 R |
| 5,132,012 A | 7/1992 | Miura et al. | 210/198.2 |
| 5,194,133 A | 3/1993 | Clark et al. | 204/299 R |
| 5,571,398 A | 11/1996 | Karger | 204/603 |
| 5,571,410 A | 11/1996 | Swedberg et al. | 210/198.2 |
| 5,658,413 A | 8/1997 | Kaltenbach et al. | 156/272.8 |
| 5,779,868 A * | 7/1998 | Parce et al. | 204/604 |
| 6,008,980 A * | 12/1999 | Stevenson et al. | 361/302 |
| 6,033,628 A * | 3/2000 | Kaltenbach et al. | 422/68.1 |

FOREIGN PATENT DOCUMENTS

| | | | |
|---|---|---|---|
| WO | WO 97/04297 | 6/1997 | G01N/30/04 |
| WO | WO 87/26072 | 7/1997 | B01D/49/00 |

OTHER PUBLICATIONS deCastro et al., "Minaturisation: A Well–Defined Trend in Separation and Preconcentration Techniques," Analytica Chemica Acta 351(1–3):23–40 (1997).
Dijkstra et al., "An Eluent–Jet Interface for Chemical Ionization Mass Spectrometry and Coupling of Microcolumn Liquid Chromatography with Electron Ionization Mass Spectrometry," Rapid Communications in Mass Spectrometry 12(1):5–10 (1998).
Fan, Anal. Chem. 66:177–184 (1994).
Figeys et al., "A Microfabricated Device for Rapid Protein Identification by Microelectrospray Ion Trap Mass Spectrometry," Anal. Chem. 69:3153–3160 (1997).
Harrison, Sensors and Actuators B B 10(2):107–116 (1993).
Henry, "Micro Meets Macro: Interfacing Microchips and Mass Spectrometers," Anal. Chem. News & Lectures pp. 359A–361A (1997).
Karger et al., "Recent Developments in Microscale Mass Spectrometry," Abstracts of Papers of the American Chemical Society 214:146 (1997).

(List continued on next page.)

*Primary Examiner*—John R. Lee
*Assistant Examiner*—David A. Vanore

(57) ABSTRACT

A miniaturized planar device is described for use in a liquid phase analysis system. The device comprises a separation compartment that is in fluidic communication with a make-up flow channel and a channel compartment that terminates in an on-device mass spectrometer delivery means. The device is formed by microfabrication of microstructures in novel support substrates.

54 Claims, 7 Drawing Sheets

OTHER PUBLICATIONS

Kebarle, P. and Tang, L., "From Ions in Solution to Ions in the Gas Phase: The Mechanism of Electrospray Mass Spectrometry," Analytical Chemistry 65(22):972A–986A (1993).

König, S. and Fales, H.M., "Comment on the Cylindrical Capacitor Electrospray Interface," Analytical Chemistry 2.9:pp A–C (1998).

Manz, Trends Anal. Chem. 10:144–149 (1991).

Manz, Adv. In Chrom. 33:1–66 (1993).

Manz, Sensors and Actuators B B1(1–6):249–255 (1990).

Ramsey, R.S. and Ramsey, J.M., "Generating Electrospray From Microchip Devices Using Electroosmotic Pumping," Anal. Chem. 69:1174–1178 (1997).

Wang, H. and Hackett, M., "Ionization Within a Cylindrical Capacitor: Electrospray Without an Externally Applied High Voltage," Anal. Chem. 70:205–212 (1998).

Wilm, M. and Mann, M., "Analytical Properties of the Nanoelectrospray Ion Source," Anal. Chem. 68:1–8 (1996).

Xue et al., "Integrated Multichannel Microchip Electrospray Ionization Mass Spectrometry: Analysis of Peptides From On–Chip Tryptic Digestion of Melittin," Rapid Communications in Mass Spectrometry 11(12):1253–1256 (1997).

Xue et al., "Multichannel Microchip Electrospray Mass Spectrometry," Analytical Chemistry 69(3):426430 (1997).

"Preliminary Product Information Specialty Fused–Silica Tips," New Objective Inc. Catalog, 6 pages (1998).

\* cited by examiner

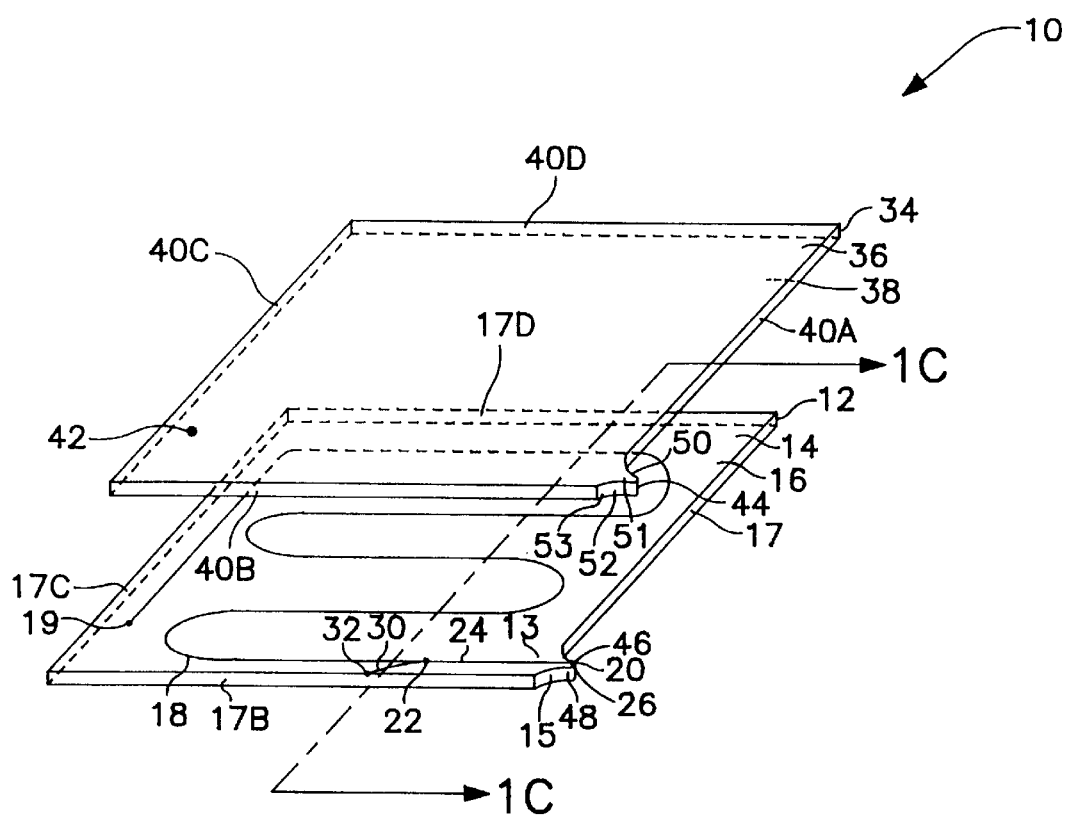
FIG. IA

MINIATURIZED DEVICE FOR SEPARATING THE CONSTITUENTS OF A SAMPLE AND DELIVERING THE CONSTITUENTS OF THE SEPARATED SAMPLE TO A MASS SPECTROMETER

CROSS-REFERENCE TO RELATED APPLICATIONS

This application is related to provisional patent application Ser. No. 60/089,033, filed Jun. 12, 1998, from which priority is claimed under 35 USC §119(e)(1) and which is incorporated herein by reference in its entirety.

TECHNICAL FIELD

The present invention relates generally to the miniaturized liquid phase sample processing and analysis. More particularly, the invention relates to a miniaturized planar separation device with a means of delivering sample constituents to a mass spectrometer (MS).

BACKGROUND

Sensitive identification of analytes in a complex sample matrix is difficult, and requires careful thought as to (a) the preparation of the sample for MS analysis (i.e., detergents, buffer salts, etc.), (b) whether a separation step is required to simplify the complexity of the sample for MS analysis, and (c) whether additional sample processing (i.e., chemical, enzymatic, affinity capture, etc.) is required to generate the desired information from the MS analysis of the sample. An ideal device would allow rapid detection of a wide range of simple or complex molecules in the liquid phase, at relevant concentrations, and yield information about the molecule's molecular mass. Additional chemical structural information may be gained by employing a tandem MS technique, such as, but not necessarily limited to Quadrupole Time-of-Flight tandem MS or Ion Trap MS. A desirable feature of the detection method would be to enable the separation criteria to be relaxed such that the separation and detection could occur in series, without the need for high-efficiency, high-end separation technology, such as standard high performance liquid chromatography equipment. The orthogonality of MS analysis to liquid-based separation techniques helps make this possible. An on-line detector is particularly advantageous when sample size is limited, high throughput is required, and automation is desired. Moreover, MS detection methods are well suited to yield high quality chemical information for multi-component samples, requiring no a priori knowledge of the constituents.

Though much has been discussed in the literature towards realizing integrated separation technology including sample preparation and separation devices, and associated fluidics so that low yield or precious samples may be prepared and analyzed, little has been realized to date. In sample analysis instrumentation, particularly in separation systems involving capillary electrophoresis or liquid chromatography, smaller dimensions of the separation compartments result in improved performance characteristics, while reducing cost of analysis and production. Miniaturization of the separation region, to result in small sample volume requirements, necessarily means a greater demand on the detection method both by virtue of sample volume and potentially, sensitivity.

There are many types of detection methods possible. Optical transmission methods such as refractive index, ultraviolet-visible (UV-VIS) and infrared (IR) are relatively inexpensive, but are unable to give complex chemical structural information. Furthermore, they are path-length limited and sensitivity of detection is limited. Infrared spectroscopy is relatively insensitive, particularly to contaminants, and yields only functional group or fingerprint identification. MS is a sensitive method providing mass information and tandem MS can provide detailed structural information.

The sensitivity of analysis with conventional separation methods for on-line mass spectrometric detection typically suffers from adsorptive sample loses and from sample contamination during sample handling procedures. The development of microfluidic devices for separation coupled with delivery to an electrospray ionization mass spectrometer holds the promise to greatly increase analysis sensitivity by minimizing the complexity of the interface by incorporating features such as make-up flow elements, on-device metallization, and on-device fluidic interconnect features that readily allow for zero dead-volume incorporation of make-up flow elements or MS transfer lines. Additionally, higher sample throughputs are possible, as the scale of any microfluidic device is much smaller, and consequently faster, than currently existing conventional-scale fluidic devices.

SUMMARY OF THE INVENTION

The present invention relates to a miniaturized planar device, which can be used in a liquid phase analysis system. It is a primary object of the invention to provide a miniaturized device that has been microfabricated in a substantially planar substrate. The analytical device generally has at least one separation component, which is adapted for a direct, on-line coupling to an associated mass spectrometer.

In one embodiment of the invention, a miniaturized device is provided. The device comprises (a) a substrate having first and second substantially planar opposing surfaces and lateral surfaces substantially perpendicular to the planar surfaces, wherein the substrate has a first microchannel having an interior surface and a second microchannel having an interior surface in the first planar surface, (b) a cover plate arranged over the first planar surface having first and second substantially planar opposing surfaces and lateral end surfaces substantially perpendicular to the planar surfaces, wherein (i) the first surface of the cover plate in combination with the first microchannel forms a separation compartment having first and second termini and (ii) the first surface of the cover plate in combination with the second microchannel forms a channel compartment having first and second termini, and further wherein the second terminus of the separation compartment and the first terminus of the channel compartment are coterminus, (c) an inlet port in fluid communication with the first terminus of the first microchannel and a make-up flow port in fluid communication with the second terminus of the first microchannel, respectively, wherein the inlet port enables the passage of fluid from a first source through the separation compartment, and the make-up flow port enables the passage of fluid from a second source through a make-up flow channel in fluid communication the second terminus of the separation compartment and a channel compartment having first and second termini, wherein the first terminus of the channel compartment is in fluid communication with the second terminus of the separation compartment and second terminus of the channel compartment is in fluid communication with an on-device mass spectrometer delivery means.

These and other embodiments of the subject invention will readily occur to those of ordinary skill in the art in view of the disclosure herein.

BRIEF DESCRIPTION OF THE FIGURES

FIG. 1 illustrates one embodiment of the miniaturized device constructed in accordance with the disclosure herein in which the on-device mass spectrometer delivery means comprises a nozzle formed from projections in the lateral surfaces of a substrate and a cover plate. FIG. 1A is a perspective view of an embodiment with a microchannel in the surface of a substrate which, in combination with a cover plate forms a separation compartment.

FIG. 2 illustrates another embodiment of the invention in which the on-device mass spectrometer delivery means comprises a nozzle formed in the cover plate or the substrate.

FIG. 3 illustrates another embodiment of the invention in which the on-device mass spectrometer delivery means comprises a nozzle formed in the microchannel.

FIG. 4 illustrates yet another embodiment of the invention in which the on-device mass spectrometer delivery means is an on-device transfer line.

FIG. 5 illustrates metallization layers formed on the device.

DETAILED DESCRIPTION OF THE INVENTION

Figure 1B:
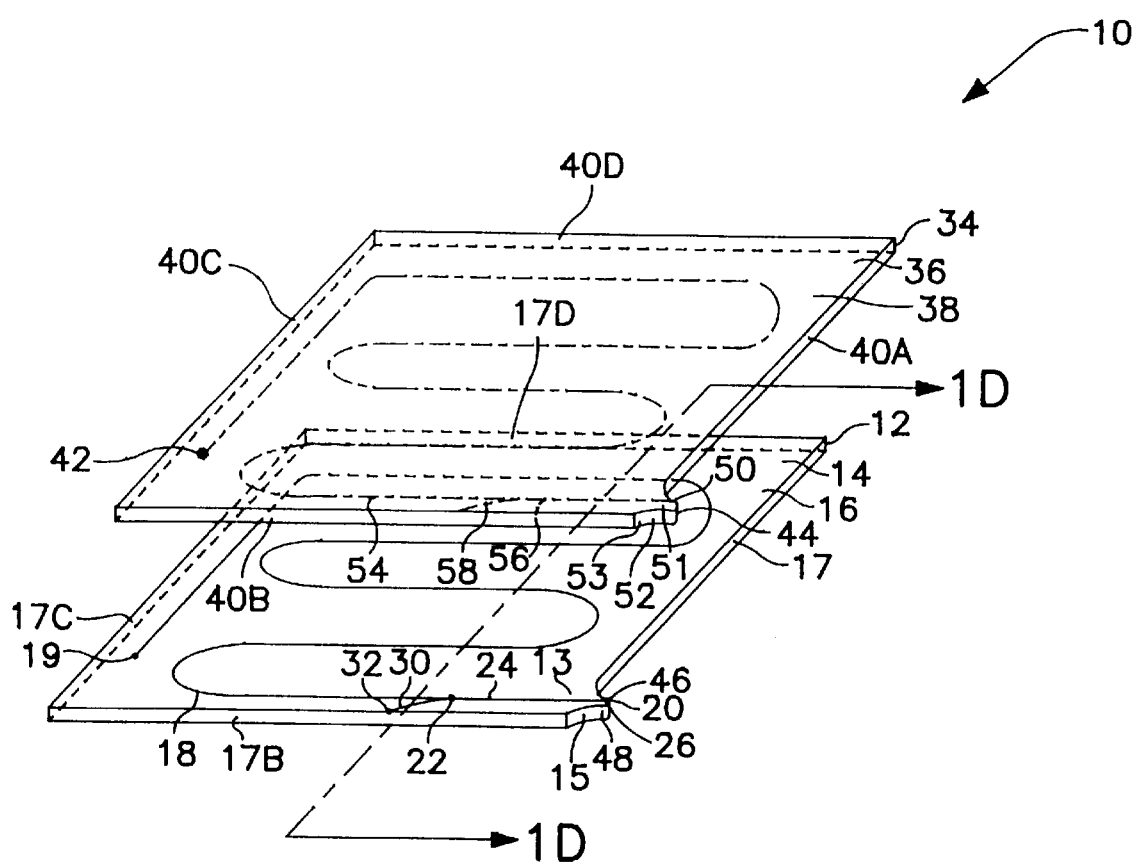
FIG. 1B is a perspective view of an embodiment with first and second microchannel in the surface of the substrate and the cover plate, respectively, which, in combination forms a separation compartment.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, and the like.

In this specification and in the claims, which follow, reference will be made to a number of terms, which shall be defined to have the following meanings:

The term "substrate" as used herein refers to any material that can be microfabricated, e.g., dry etched, wet etched, laser etched, molded or embossed, to have desired miniaturized surface features. In addition, microstructures can be formed on the surface of a substrate by adding material thereto, for example, polymer channels can be formed on the surface of a glass substrate using photo-imageable polyimide. Preferably, the substrate is capable of being microfabricated in such a manner as to form features in, on and/or through the surface of the substrate. The substrate can be a polymer, a ceramic, a glass, a metal, a composite thereof, a laminate thereof, or the like. Polymer materials are particularly preferred. Polymer materials include materials selected from the following examples, but not limited to: polyimide, polycarbonate, polyester, polyamide, polyether, polyolefin, polymethyl methacrylates, polyurethanes, poly (acrylonitrile-butadiene-styrene) (ABS) copolymers, polystyrene, polyfluorcarbons, or mixtures thereof.

Microanalysis devices and systems comprising such devices are prepared using suitable substrates as described above. A "composite" is a composition comprised of unlike materials. The composite may be a block composite, e.g., an A-B-A block composite, an A-B-C block composite, or the like. Alternatively, the composite may be a heterogeneous, i.e., in which the materials are distinct or in separate phases, or homogeneous combination of unlike materials. As used herein, the term "composite" is used to include a "laminate" composite. A "laminate" refers to a composite material formed from several different bonded layers of same or different materials. Other preferred composite substrates include polymer laminates, polymer-metal laminates, e.g., polymer coated with copper, a ceramic-in-metal or a polymer-in-metal composite.

The microstructures in the miniaturized separation device of the invention, e.g., separation compartments, make-up flow channel and channel compartment, MS nozzles, injection means, and micro-alignment means, may be formed by microfabrication in a support body such as a polymeric, ceramic, glass, metal or composite substrate.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

The term "injection molding" is used to refer to a process for molding plastic or nonplastic ceramic shapes by injecting a measured quantity of a molten plastic or ceramic substrate into dies (or molds). In one embodiment of the present invention, miniaturized devices can be produced using injection molding.

The term "embossing" is used to refer to a process for forming polymer, metal or ceramic shapes by bringing an embossing die into contact with a preexisting blank of polymer, metal or ceramic. A controlled force is applied between the embossing die and the pre-existing blank of material such that the pattern and shape determined by the embossing die is pressed into the pre-existing blank of polymer, metal or ceramic. The term "hot embossing" is used to refer to a process for forming polymer, metal, or ceramic shapes by bringing an embossing die into contact with a heated pre-existing blank of polymer, metal, or ceramic. The pre-existing blank of material is heated such that it conforms to the embossing die as a controlled force is applied between the embossing die and the pre-existing blank. The resulting polymer, metal, or ceramic shape is cooled and then removed from the embossing die.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated at high energy radiation using a synchrotron source to create desired microstructures (such as channels, ports, apertures and micro-alignment means), thereby forming a primary template.

It will be readily apparent to one of ordinary skill in the art that microfabrication techniques may be used to form miniaturized sample processing channels and apertures in a wide variety of geometries.

The term "separation compartment" is used herein to refer to a microfabricated region of the support in which sample separation, preferably analytical sample separation, is carried out. "Analytical separation" is defined as the final separation means of analyte from minor components before final analyte detection. In particular, an analyte of interest is generally obtained in a matrix containing other species which may potentially interfere with the detection and analysis of the analyte. Accordingly, a separation compartment is a region of the support in which analyte separation from other species is effected. Examples of functions which may be served by the sample treatment component include chromatographic separations, electrophoretic separations, electrochromatographic separations, and the like.

The term "channel compartment" is used herein to refer to a microfabricated region of the support in which analyte, having been mixed with make-up flow medium, is transported to a mass spectrometer injection means as defined herein.

The term "make-up flow channel" is used herein to refer to a microfabricated region of the support in fluidic communication with a source of make-up flow media and by which the make-up flow media is transferred to the terminus of the separation compartment.

The term "dead volume" refers to undesirable voids, hollows or gaps created by the incomplete engagement, sealing or butting of a port with a fluid line affixed thereto.

The term "connector port" is used herein to refer to a microfabricated region of the support or cover plate, or a portion of the support and a portion of the cover plate in combination that provides a sleeve in which an off-device fluid line, e.g., a capillary tube or the like, can be affixed to provide a zero dead-volume or low dead-volume connection between the inner diameter of the fluid line and the on-device fluidic port.

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography, affinity chromatography and like methods.

"Electrophoretic" separations refers to the migration of particles or macromolecules having a net electric charge where said migration is influenced by an electric field. Accordingly electrophoretic separations contemplated for use in the invention include separations performed in columns packed with gels (such as poly-acrylamide, agarose and combinations thereof) as well as separations performed in solution.

"Electrochromatographic" separations refer to combinations of electrophoretic and chromatographic techniques. Electrochromatographic separations is a hybrid technique typically performed in microcapillary format. Column packing may be either traditional packed column (see, e.g., Knox et al. (1987) *Chromatographia* 24:135) or monolithic packing (see, e.g., Peters et al. (1998) *Anal. Chem.* 70:2288).

The term "motive force" is used to refer to any means for inducing movement of a sample along a column in a liquid phase analysis, and includes application of an electric potential across any portion of the column, application of a pressure differential across any portion of the column or any combination thereof.

The term "surface treatment" is used to refer to preparation or modification of the surface of a substrate that will be in contact with a sample during separation, whereby the separation characteristics of the device are altered or otherwise enhanced. Accordingly, "surface treatment" as used herein includes: physical surface adsorptions; covalent bonding of selected moieties to functional groups on the surface of treated substrates (such as to amine, hydroxyl or carboxylic acid groups on condensation polymers); methods of coating surfaces, including dynamic deactivation of treated surfaces (such as by adding surfactants to media), polymer grafting to the surface of treated substrates (such as polystyrene or divinyl-benzene) and thin-film deposition of materials such as diamond or sapphire to treated substrates.

The term "plurality" as used herein is intended to mean two or more.

"Optional" or "optionally" means that the subsequently described feature or structure may or may not be present in the integrated planar separation device or that the subsequently described event or circumstance may or may not occur, and that the description includes instances where said feature or structure is present and instances where the feature or structure is absent, or instances where the event or circumstance occurs and instances where it does not. For example, the phrase "a microanalysis device optionally having metallization" intends that metallization may or may not be present on the device and that the description includes both circumstances where metallization are present and absent.

The invention, together with additional features and advantages thereof, may be best understood by reference to the following description taken in connection with the illustrative drawings.

With reference to FIG. 1A and FIG. 1B, a microanalysis device (10) is generally provided. The device comprises a substrate (12) having first (14) and second (16) substantially planar opposing surfaces, first, second, third and fourth lateral surfaces (17A, 17B, 17C, and 17D), a first microchannel (18) having first (19) and second (22) termini microfabricated in the first planar surface of the substrate, a second microchannel (24) having first terminus that is coterminus with the second terminus (22) of the first microchannel and second terminus (26) microfabricated in the first planar surface of the substrate, a third microchannel (30) having a first terminus (32) and a second terminus that is coterminus with the second terminus (22) of the first microchannel, and a projection (20) protruding from the first lateral surface of the substrate having first (46) and second (48) exterior surfaces contiguous with the lateral surface of the substrate, and first (13) and second (15) substantially planar opposing surfaces contiguous with the first (14) and second (16) substantially planar opposing surfaces, respectively. It will be readily appreciated that, although the microchannel (18) has been represented in a generally extended form, microchannels formed under the invention may be microfabricated in a large variety of configurations, such as a straight, serpentine, spiral, or any tortuous path desired. Further, microchannel (18) may be formed in a wide variety of channel geometries including semi-circular, rectangular, rhomboid, and the like, and the channels may be formed in a wide range of aspect ratios. It is also noted that a device having a plurality of microchannels microfabricated therein falls within the spirit of the present invention.

Figure 1C:
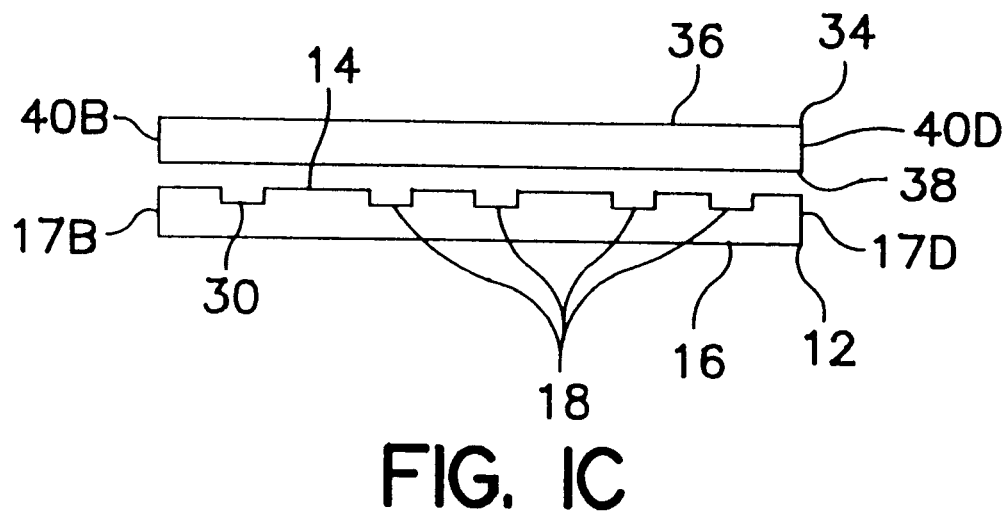
FIG. 1C is a cross-section view of FIG. 1A.

Cover plate (34) having first (36) and second (38) substantially planar opposing surfaces, first, second, third and fourth lateral surfaces (40A, 40B, 40C, and 40D), port (42) and projection (44) protruding from the first lateral surface of the cover plate having first (50) and second (52) exterior surfaces contiguous with the lateral surface of the cover plate, and first (51) and second (53) substantially planar opposing surfaces contiguous with the first (36) and second (38) substantially planar opposing surfaces, respectively, is arranged over first planar surface (14) of substrate (12) and, in combination with (a) first microchannel (18) forms an elongate separation compartment, (b) second microchannel (24) forms a channel compartment and (c) third microchannel (30) forms a make-up flow channel. Furthermore, projection (44) in cover plate (34) in combination with projection (20) in substrate (12) form an on-device MS delivery means which, in FIG. 1 is depicted as a nozzle.

The separation compartment has the following dimensions: about 10 $\mu$m to about 250 $\mu$m, preferably about 50 $\mu$m to about 200 $\mu$m internal diameter.

The nozzle dimensions are about 1 $\mu$m to about 200 $\mu$m, preferably about 5 $\mu$m to about 100 $\mu$m internal diameter and about 5 $\mu$m to about 300 $\mu$m, preferably about 5 to about 100 $\mu$m outside diameter.

The channel compartment has the same internal diameter dimension as the internal diameter of the port from the protruding nozzle, i.e., from about 1 $\mu$m to about 200 $\mu$m, preferably about 5 $\mu$m to about 100 $\mu$m.

The make-up flow channel has the following dimensions: about 10 $\mu$m to about 250 $\mu$m, preferably about 50 $\mu$m to about 200 $\mu$m internal diameter.

Port (42) is situated in cover plate (34) such that, when the cover plate is removably or fixably aligned over first planar surface (14) of substrate (12), port (42) is in fluid communication with first terminus (19) of first microchannel (18), enabling passage of fluid from an external source into the separation compartment. Cover plate (34) may be formed from any suitable substrate such as a polymer, a ceramic, a glass, a metal, a composite thereof, a laminate thereof, or the like.

Although illustrated as a separate component, it will be recognized by a person of skill in the art that the cover plate may be hingeably affixed to the substrate, as illustrated in FIGS. 5, 8A, 8B, 11 of U.S. Pat. No. 5,658,413 to Kaltenbach et al.

Cover plate (34) may be removably or fixably aligned over the first planar surface (14) of substrate (12) to form a liquid-tight separation compartment by using pressure sealing techniques, by using external means to urge the pieces together (such as clips, tension springs or associated clamping apparatus) or by using adhesives well known in the art of bonding polymers, ceramics, glass, metal, composites, laminates, and the like.

The second terminus (32) of the third microchannel (30) is a port connector in lateral surface (17) of substrate (12) enabling passage of make-up flow medium from an external source into the make-up flow channel and then into the channel compartment through terminus (22). Alternatively, as illustrated in FIGS. 1 and 2 of International Publication No. WO 96/12546, published May 2, 1996 (inventors Kaltenbach et al.), the second terminus (32) of third microchannel (30) can be in fluid communication with an on-device reservoir from which make-up flow medium can be transferred into the channel compartment.

Figure 1D:
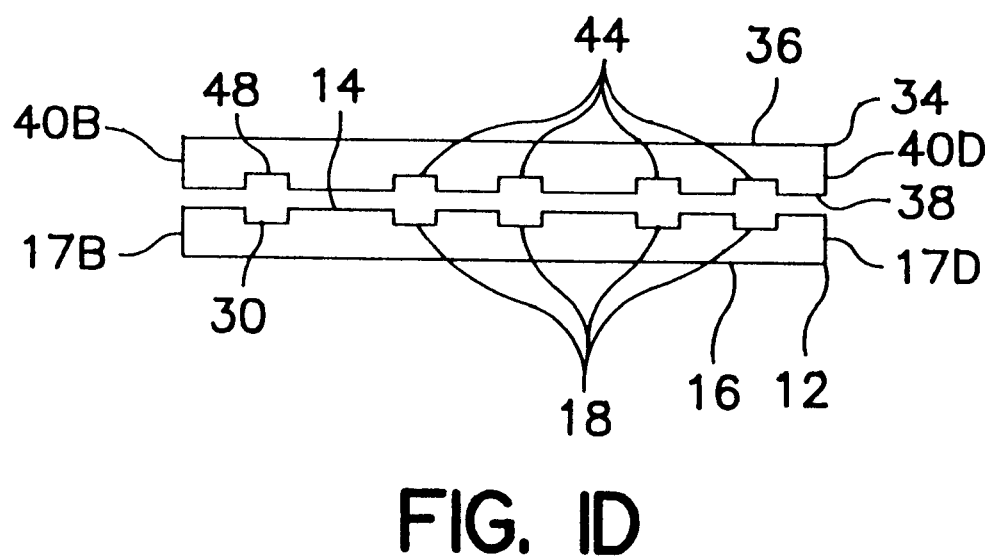
FIG. 1D is a cross-section view of FIG. 1B.

In another embodiment, illustrated in FIG. 1B and FIG. 1D, fourth (54), fifth (56) and sixth (58) microchannels, which are mirror images of first (18), second (24) and third (30) microchannels, respectively, are microfabricated first planar surface (38) of cover plate (34), as illustrated in FIG. 11 of U.S. Pat. No. U.S. Pat. No. 5,658,413, supra. Upon removable or fixable alignment of cover plate (34) with substrate (12), the separation compartment, channel compartment and make-up flow compartment are formed by alignment of first microchannel (18), second microchannel (24) and third microchannel (30) with fourth microchannel (54), fifth microchannel (56) and sixth microchannel (58), respectively.

Figure 2A:
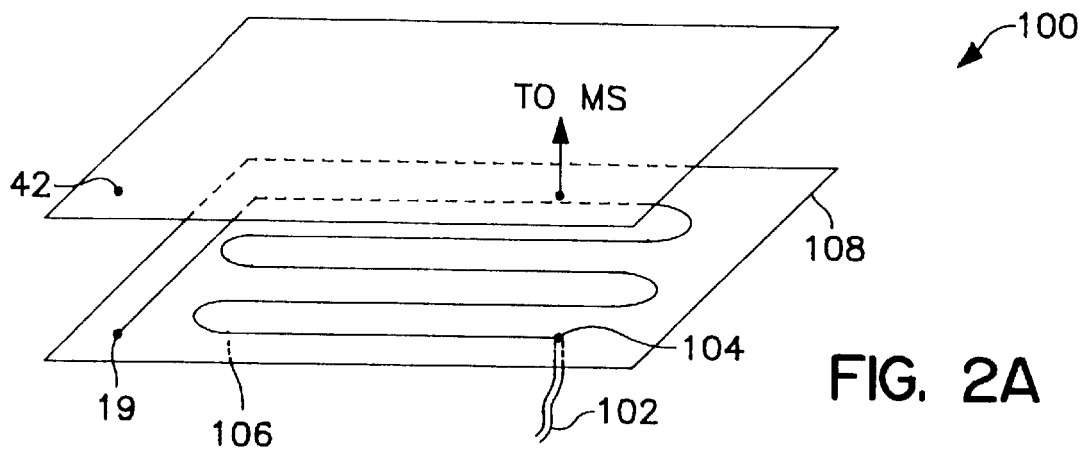
FIG. 2A is a perspective view showing the cover plate and substrate.
Figure 2B:
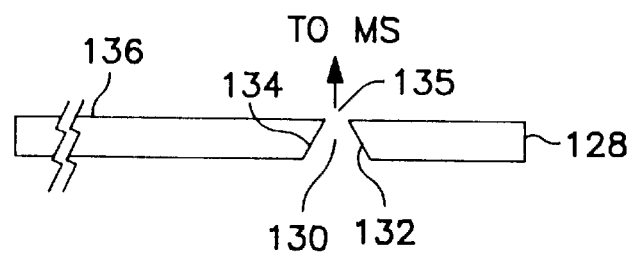
FIG. 2B is a cross-section view illustrating one configuration of the nozzle.
Figure 2C:
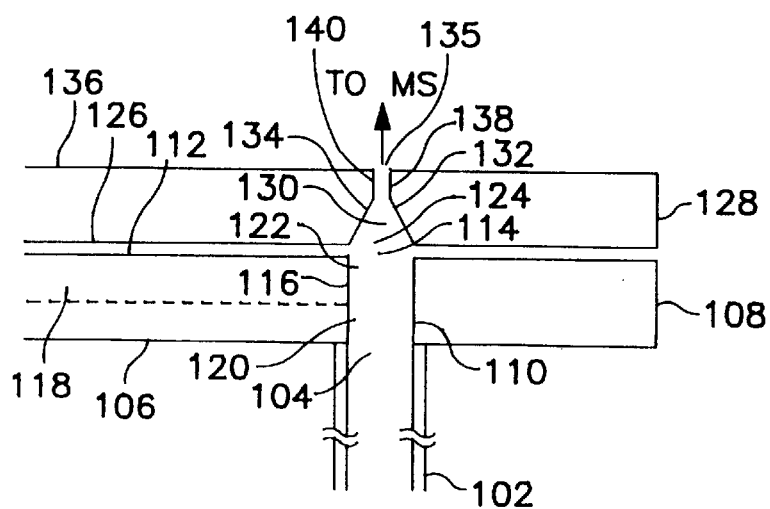
FIG. 2C is a cross-section view illustrating another configuration of the nozzle.

An alternate embodiment of the device utilizing a distinct configuration of on-device MS delivery means is illustrated in FIG. 2A, FIG. 2B and FIG. 2C. The device, generally illustrated at 100 comprises a fluidic line 102 affixed to a make-up flow port 104 which is an aperture in the second surface 106 of substrate 108. Make-up flow port 104 forms the first end of bore 110 that extends from the second surface 106 to the first surface 112 of substrate 108 and terminates in nozzle port 114. Bore 110 form a fluidic interconnection 116 with separation compartment 118 formed in the first surface 112 of substrate 108. In this embodiment, the make-up flow channel 120 extends from make-up flow port 104 to interconnection 116 and the channel compartment 122 extends from interconnection 116 to nozzle port 114. In this embodiment, the nozzle is formed as a tapered bore in the cover plate as follows. Aperture 124 in the first surface 126 of cover plate 128 forms the first end of bore 130. Bore 130 has tapered sides 132 and 134. As illustrated in FIG. 2B, the tapered sides 132, 134 of bore 130 extend to aperture 135 in the second surface 136 of cover plate 128. Alternatively, as illustrated in FIG. 2C, the tapered sides 132, 134 can terminate at a section of bore 130 having essentially parallel sides 138, 140. One of skill in the art will recognize that the MS nozzle can be formed in the substrate and that the make-up flow port, make-up flow channel, channel compartment and separation compartment can be formed in the cover plate.

The tapered nozzle illustrated in FIG. 2C has the following dimensions: the widest part of the nozzle is from about 20 $\mu$m to about 50 $\mu$m and the exit port in the upper surface is about 8 $\mu$m to about 30 $\mu$m.

Figure 3A:
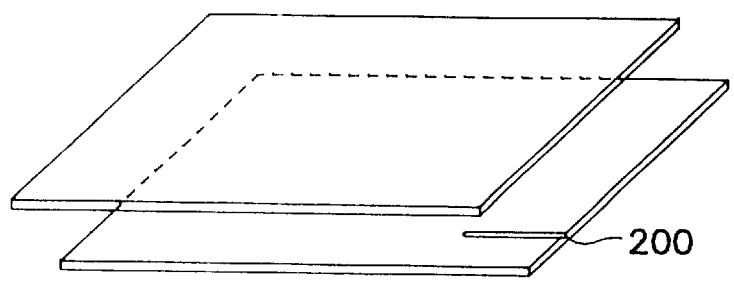
FIG. 3A is a perspective view illustrating the cover plate, substrate, microchannel and the nozzle in the microchannel.
Figure 3B:
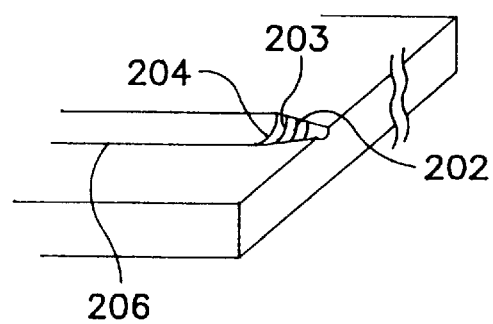
FIG. 3B is an exploded view illustrating the substrate, the microchannel formed therein and the nozzle.
Figure 3C:
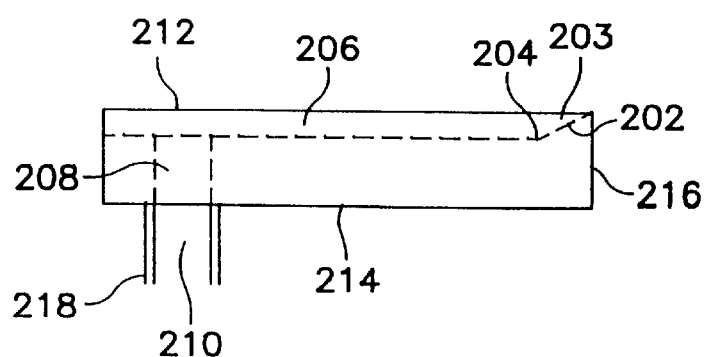
FIG. 3C is a cross-section view illustrating the nozzle formed in the channel and an embodiment of the make-up flow channel.

Yet another alternate embodiment of the device utilizing a distinct on-device MS delivery means is illustrated in FIG. 3A, FIG. 3B and FIG. 3C. The device is generally indicated at 200 and comprises nozzle 202 having interior surface 203 that is formed in at the second terminus 204 of the channel compartment 206. For purposes of illustration only, the make-up flow channel is shown in FIG. 3C as a bore 208 extending from make-up flow port 210 in the first surface 212 to the second surface 214 of the substrate 216. Also illustrated in FIG. 3C is a make-up flow fluid line 218 butt-coupled to the second surface 214 of substrate 216 at make-up flow port 210.

Figure 4A:
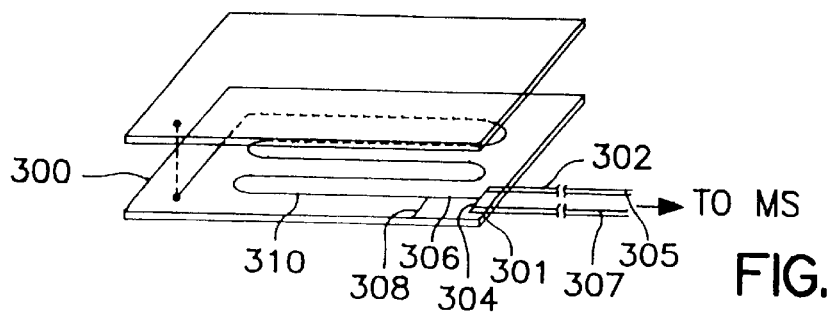
FIG. 4A is a perspective view illustrating a cover plate, a substrate with a microchannel formed therein and an on-device transfer line.
Figure 4B:
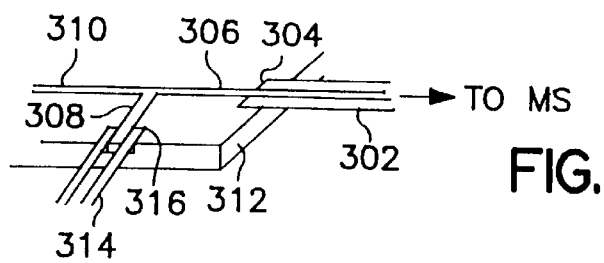
FIG. 4B is an exploded view of the device illustrating the on-device transfer line and an embodiment of the make-up flow line.
Figure 4C:
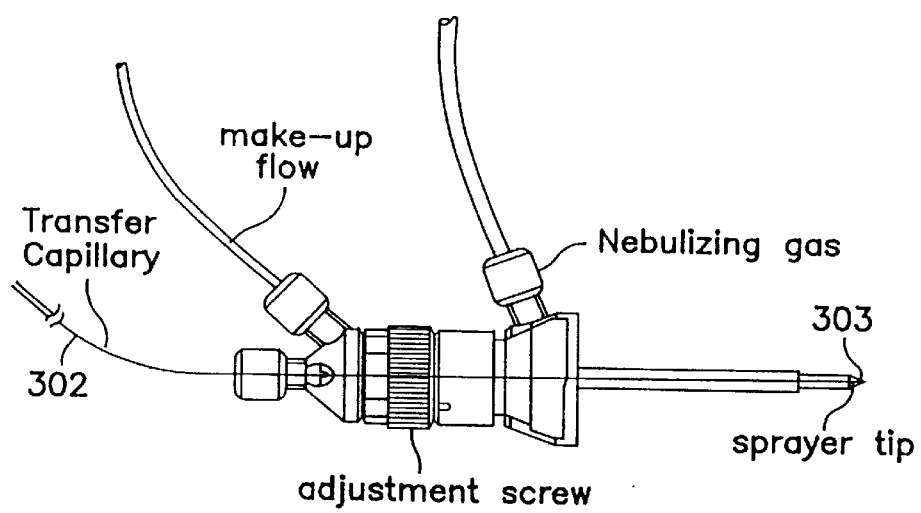
FIG. 4C is a cross-section view of a traditional interface from the transfer line to the MS inlet.
Figure 4D:
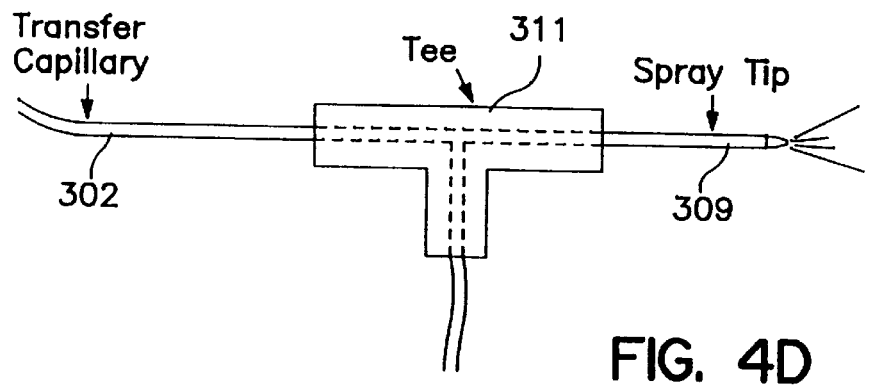
FIG. 4D is an alternative interface design comprising a transfer capillary coupled to a spray tip through a tee.
Figure 5A:
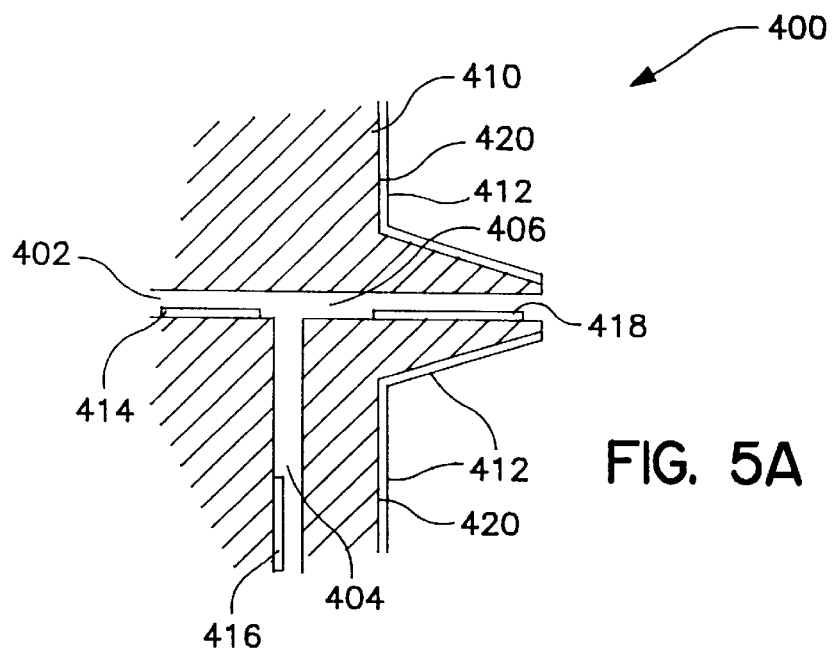
FIG. 5A is a cross-section view illustrating metallization layers on the external lateral surface of the substrate, in the separation compartment, in the make-up flow channel, and in the channel compartment (not to scale).
Figure 5B:
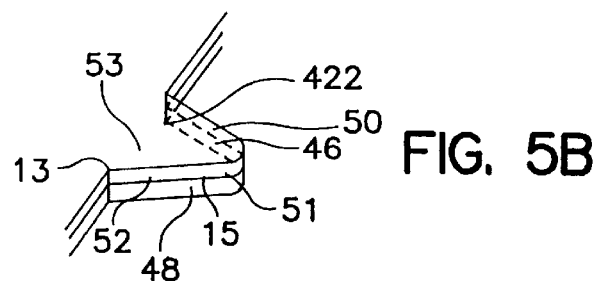
FIG. 5B is a perspective view of metallization layers on the nozzle formed as a combination of projections from the lateral surfaces of the substrate and the cover plate.
Figure 5C:
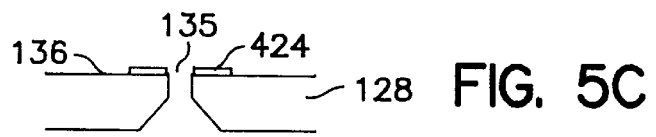
FIG. 5C and FIG. 5D are cross-section and top views, respectively, of a metallization layer formed as a contiguous layer surrounding aperture as illustrated in FIG. 2.
Figure 5D:
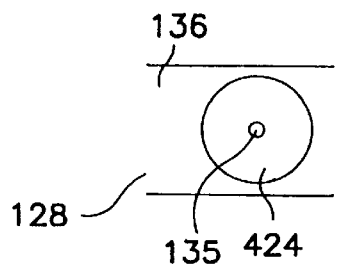
Figure 5E:
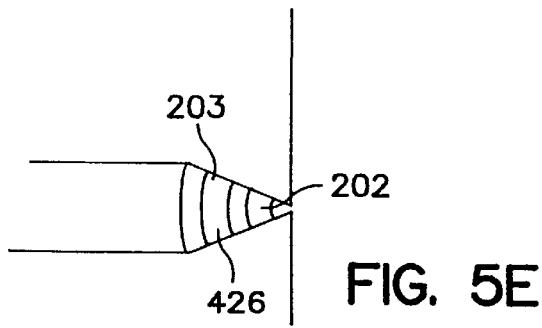
FIG. 5E is a top view of that a metallization layer placed on the interior surface of the nozzle as illustrated in FIG. 3.

Still another embodiment of the device utilizing an third distinct on-device MS delivery means is illustrated in FIG. 4A and FIG. 4B. The device, generally indicated at 300, comprises transfer line 302 having a first end 301 affixed to the second terminus 304 of channel compartment 306, second end 303 located at the MS inlet and inner 305 and outer 307 surfaces. One traditional interface from the transfer line to the MS inlet consists of a triaxial design where the center tube in the transfer line, the second tube delivers the make-up fluid, and the outer-most tube delivers pressurized nebulizing gas (FIG. 4C). In this interface design, the make-up fluid is supplied coaxially. An alternative interface design is shown in FIG. 4D. In this design, the transfer capillary 302 may be coupled to a separate spray tip 309 through the use of a tee 311 where the make-up fluid is supplied through the center port of the tee.

Make-up flow channel 308 is in fluid communication with channel compartment 306 and separation compartment 310 as described above. In one embodiment, illustrated in FIG. 4B, transfer line 302 is affixed to the substrate 312 at the second terminus 304 of channel compartment 306 using a connector port. Alternatively, transfer line 302 can be affixed to the substrate 312 using a butt coupling. The transfer line can be a fuse silica capillary or a polymeric capillary material, e.g., polyimide, urethane, nylon, polyetheretherketone (PEEK), or the like. Furthermore, in one embodiment, make-up flow fluid line 314 is affixed to make-up flow port 316 using a connector port. However, make-up flow fluid line 314 can be affixed to substrate 312 at make-up flow port 316 using a butt coupling.

The connector port is dimensioned to be capable of accepting tubing having an outer diameter of about 100 μm to about 500 μm, preferably about 50 μm to about 250 μm. Butt-coupled tubing typically has dimensions, e.g., of about 50 μm to about 2 mm internal diameter and about 100 μm to about 3 mm outer diameter.

In order to deliver sample from the device to an MS, a complete electrical circuit is required: there must be a potential difference between the MS inlet and the on-device MS delivery means. Two common configurations of MS inlet are know: one in which the MS inlet is at a set potential; and one a which the MS inlet is at ground. Accordingly, in order to create a complete electrical circuit through the fluidic device the MS delivery means is metallized with a metallization layer for connection to a voltage source or ground. The MS delivery means and make-up fluid together are placed either at ground, if the MS inlet is at potential, or at set potential, if the MS inlet is at ground. To enhance electrical contact with the fluid in the circuit in order to create a more stable means of ionization, a metallization layer may be deposited on the interior surface of end of the separation channel, on the interior surface of the make-up flow channel or on the interior surface of the channel compartment proximal to the nozzle port. As previously described in the case of the metallization of the external portion of the nozzle in the above example, the metallized layer and make-up fluid are set at potential if the MS inlet is at ground, and vice versa. Finally, the combination of the metallized exterior surface, and metallization on the interior of either the separation channel, make-up flow channel or channel compartment is still another desired configuration. In this embodiment, the metallized surfaces and make-up flow are set at a potential if the MS inlet is grounded and vice versa.

FIG. 5 illustrates metallization layers formed as described above. Thus, in FIG. 5A, a device, generally indicated at 400 comprises separation compartment 402, make-up flow compartment 404, channel compartment 406 and on-device MS delivery means shown as a nozzle 408 in substrate 410 are illustrated. As described above, first 412, second 414, third 416 and fourth 418 metallization layers are situated on external lateral surface 420 of substrate 410, in separation compartment 402, in make-up flow compartment 404, or channel compartment 406, respectively. In the embodiment of the device illustrated in FIG. 1, in which the on-device delivery means is a nozzle formed by a combination of the projection in the lateral surface of the substrate and the projection in the lateral surface of the cover plate, and as illustrated in FIG. 5B, it is preferred that the nozzle comprises a metallization layer 422 on the first (46) and second (48) exterior surfaces contiguous with the lateral surface of the substrate, on the first (50) and second (52) exterior surfaces contiguous with the lateral surface of the cover plate, the first (13) and second (15) substantially planar opposing surfaces of the projection in the substrate, the first (51) and second (53) substantially planar opposing surfaces of the projection in the cover plate, and at least a portion of the lateral surfaces of the substrate and cover plate adjacent to the projections therein. In the embodiment of the device illustrated in FIG. 2, and as illustrated in FIG. 5C and FIG. 5D, it is preferred that a contiguous metallization layer 424 is placed on the second surface 136 of cover plate 128 surrounding aperture 135. In the embodiment illustrated in FIG. 3, and as illustrated in FIG. 5E, it is preferred that a metallization layer 426 is placed on the interior surface 203 of nozzle 202. In the embodiment illustrated in FIG. 4, the metallization layer is placed on the outer surface 307 of the second terminus 303 of transfer line 302.

We claim:

1. A miniaturized device comprising:
   (a) a substrate having first and second substantially planar opposing surfaces and lateral surfaces substantially perpendicular to the planar surfaces, wherein the substrate has a first microchannel having an interior surface and a second microchannel having an interior surface in the first planar surface;
   (b) a cover plate having first and second substantially planar opposing surfaces and lateral end surfaces substantially perpendicular to the planar surfaces of the cover plate, wherein (i) the cover plate is arranged over the substrate such that the first surface of the cover plate in combination with the first microchannel forms a separation compartment having first and second termini and (ii) the first surface of the cover plate in combination with the second microchannel forms a channel compartment having first and second termini, and further wherein the second terminus of the separation compartment and the first terminus of the channel compartment are coterminal;
   (c) an inlet port in fluid communication with the first terminus of the separation compartment;
   (d) a make-up flow port in fluid communication through a make-up flow channel with the second terminus of the separation compartment;
   (e) a mass spectrometer delivery means in fluid communication with the second terminus of the channel compartment, wherein the mass spectrometer delivery means has a size and shape that allow direct coupling of the mass spectrometer delivery means to an inlet of a mass spectrometer; and (f) a first metallization layer on a surface of the substrate, a surface of the cover plate or both, wherein the first metallization layer allows a potential difference to be generated between the first metallization layer and the mass spectrometer inlet effective to ionize the sample constituents before introduction into the inlet of the mass spectrometer, wherein:

the inlet port enables the passage of fluid from a first source through the separation compartment to separate a sample into sample constituents; and the make-up flow port enables the passage of fluid from a second source at a sufficient flow rate through the make-up flow channel to convey sample constituents from the second terminus of the separation compartment though the channel compartment and the mass spectrometer delivery means into the inlet of the mass spectrometer.

2. The device of claim 1, wherein the mass spectrometer delivery means comprises an MS nozzle.

3. The device of claim 1, wherein the mass spectrometer delivery means comprises an MS transfer line.

4. The device of claim 3, wherein the MS transfer line comprises a polymeric tubing.

5. The device of claim 1, wherein the make-up flow channel comprises a microchannel in the first surface of the substrate.

6. The device of claim 5, wherein the make-up flow port comprises an on-device fluidic interconnect capable of forming a zero dead-volume connection to an off-device reservoir.

7. The device of claim 5, wherein the make-up flow port is butt-coupled to a capillary tube in fluid communication with an off-device reservoir.

8. The device of claim 7, wherein the make-up flow port is in the second surface of the substrate.

9. The device of claim 7, wherein the make-up flow port is in the second surface of the cover plate.

10. The device of claim 2, wherein the MS nozzle further comprises a nozzle port in the first surface of the cover plate and a tapered first bore extending from the nozzle port to the second surface of the cover plate, the make-up flow port is in the second surface of the substrate such that the make-up flow port and the channel compartment comprise a second bore extending from the make-up flow port to a channel compartment port in the first surface of the substrate and wherein the second bore is in fluid communication with the second terminus of the separation compartment, and the nozzle port is situated over the channel compartment port.

11. The device of claim 2, wherein the MS nozzle further comprises a nozzle port in the first surface of the substrate and a tapered first bore extending from the nozzle port to the second surface of the substrate, the make-up flow port is in the second surface of the cover plate such that the make-up flow port and the channel compartment comprise a second bore extending from the make-up flow port to a channel compartment port in the first surface of the cover plate and wherein the second bore is in fluid communication with the second terminus of the separation compartment, and the nozzle port is situated over the channel compartment port.

12. The device of claim 2, wherein the MS nozzle is a tapered bore in the first planar surface of the substrate extending from the second terminus of the channel compartment to the lateral surface of the substrate.

13. The device of claim 8, wherein the MS nozzle is a tapered bore in the first planar surface of the substrate extending from the second terminus of the channel compartment to the lateral surface of the substrate.

14. The device of claim 9, wherein the MS nozzle is a tapered bore in the first planar surface of the substrate extending from the second terminus of the channel compartment to the lateral surface of the substrate.

15. The device of claim 2, wherein the substrate further comprises a first projection having first and second exterior surfaces protruding from the lateral surface of the substrate and wherein the cover plate further comprises a second projection having first and second exterior surfaces protruding from the lateral surface of the cover plate, wherein the first projection in combination with the second projection forms the MS nozzle.

16. The device of claim 1, wherein the first metallization layer provides electrical connection to ground or to potential means.

17. The device of claim 16, wherein the first metallization layer is on the interior surface of the separation compartment.

18. The device of claim 16, wherein the first metallization layer is on the interior surface of the channel compartment.

19. The device of claim 16, wherein the first metallization layer is on the interior surface of the make-up flow compartment.

20. The device of claim 10, wherein the first metallization layer is electrically contiguous and surrounds the bore in the second surface of the cover plate, and wherein the first metallization layer provides electrical connection to ground or to potential means.

21. The device of claim 20, further comprising a second metallization layer on the interior surface of the separation compartment.

22. The device of claim 20, further comprising a second metallization layer on the interior surface of the channel compartment.

23. The device of claim 20, further comprising a second metallization layer on the interior surface of the make-up flow compartment.

24. The device of claim 15, wherein the first metallization layer is electrically contiguous and surrounds the exterior surface of the MS nozzle, and wherein the metallization layer provides electrical connection to ground or to potential means.

25. The device of claim 24, further comprising a second metallization layer on the interior surface of the separation compartment.

26. The device of claim 24, further comprising a second metallization layer on the interior surface of the channel compartment.

27. The device of claim 24, further comprising a second metallization layer on the interior surface of the make-up flow compartment.

28. A miniaturized device comprising:

(a) a substrate having first and second substantially planar opposing surfaces and lateral surfaces substantially perpendicular to the planar surfaces, (b) a cover plate having first and second substantially planar opposing surfaces and lateral end surfaces substantially perpendicular to the planar surfaces, wherein the substrate has in the first planar surface thereof a first microchannel having an interior surface and a second microchannel having an interior surface, the cover plate has in the first planar surface thereof a third microchannel having an interior surface complementary to the first microchannel and a fourth microchannel having an interior surface complementary to the second microchannel, and cover plate is arranged over the substrate such that the first and third microchannels provide the mirror images of each other and such that the second and fourth microchannels provide the mirror images of each other, wherein (i) the first microchannel in combination with the third microchannel forms a separation compartment having first and second termini and (ii) the second microchannel in combination with the fourth microchannel forms a channel compartment having first and second termini, and further wherein the second terminus of the separation compartment and the first terminus of the channel compartment are coterminal;

(c) an inlet port in fluid communication with the first terminus of the separation compartment;

(d) a make-up flow port in fluid communication through a make-up flow channel with the second terminus of the first separation compartment;

(e) a mass spectrometer delivery means in fluid communication with the second terminus of the channel compartment, wherein the mass spectrometer delivery means has a size and shape that allow direct coupling of the mass spectrometer delivery means to an inlet of a mass spectrometer; and (f) a first metallization layer on a surface of the substrate, a surface of the cover plate or both, wherein the first metallization layer allows a potential difference to be generated between the first metallization layer and the mass spectrometer inlet effective to ionize the sample constituents before introduction into the inlet of the mass spectrometer, wherein:
the inlet port enables the passage of fluid from a first source through the separation compartment, and
the make-up flow port enables the passage of fluid from a second source at a sufficient flow rate through the make-up flow channel to convey sample constituents from the second terminus of the separation compartment through the channel compartment and the mass spectrometer delivery means into the inlet of the mass spectrometer.

29. The device of claim 28, wherein the mass spectrometer delivery means comprises an MS nozzle.

30. The device of claim 28, wherein the mass spectrometer delivery means comprises an MS transfer line.

31. The device of claim 30, wherein the MS transfer line comprises a polymeric tubing.

32. The device of claim 28, wherein the make-up flow channel comprises in combination a fifth microchannel having an interior surface in the first planar surface of the substrate and a sixth microchannel having an interior surface in the first planar surface of the cover plate, such that the fifth and sixth microchannels are so arranged as to provide the mirror images of each other.

33. The device of claim 32, wherein the make-up flow port comprises an on-device fluidic interconnect capable of forming a zero dead-volume connection to an off-device reservoir.

34. The device of claim 32, wherein the make-up flow port is butt-coupled to a capillary tube in fluid communication with an off-device reservoir.

35. The device of claim 34, wherein the make-up flow port is in the second surface of the substrate.

36. The device of claim 34, wherein the make-up flow port is in the second surface of the cover plate.

37. The device of claim 29, wherein
the MS nozzle further comprises a nozzle port in the first surface of the cover plate and a tapered first bore extending from the nozzle port to the second surface of the cover plate,
the make-up flow port is in the second surface of the substrate such that the make-up flow port and the channel compartment comprise a second bore extending from the make-up flow port to a channel compartment port in the first surface of the substrate and wherein the second bore is in fluid communication with the second terminus of the separation compartment, and the nozzle port is situated over the channel compartment port.

38. The device of claim 29, wherein
the MS nozzle further comprises a nozzle port in the first surface of the substrate and a tapered first bore extending from the nozzle port to the second surface of the substrate,
the make-up flow port is in the second surface of the cover plate such that the make-up flow port and the channel compartment comprise a second bore extending from the make-up flow port to a channel compartment port in the first surface of the cover plate and wherein the second bore is in fluid communication with the second terminus of the separation compartment, and the nozzle port is situated over the channel compartment port.

39. The device of claim 30, wherein the MS nozzle is a tapered bore in the first planar surface of the substrate extending from the second terminus of the channel compartment to the lateral surface of the substrate.

40. The device of claim 35, wherein the MS nozzle is a tapered bore in the first planar surface of the substrate extending from the second terminus of the channel compartment to the lateral surface of the substrate.

41. The device of claim 36, wherein the MS nozzle is a tapered bore in the first planar surface of the substrate extending from the second terminus of the channel compartment to the lateral surface of the substrate.

42. The device of claim 29, wherein the substrate further comprises a first projection having first and second exterior surfaces protruding from the lateral surface of the substrate and wherein the cover plate further comprises a second projection having first and second exterior surfaces protruding from the lateral surface of the cover plate, wherein the first projection in combination with the second projection forms the MS nozzle.

43. The device of claim 28, wherein the first metallization layer provides electrical connection to ground or to potential means.

44. The device of claim 43, wherein the first metallization layer is on the interior surface of the separation compartment.

45. The device of claim 43, wherein the first metallization layer is on the interior surface of the channel compartment.

46. The device of claim 43, wherein the first metallization layer is on the interior surface of the make-up flow compartment.

47. The device of claim 37, wherein the first metallization layer is electrically contiguous and surrounds the bore in the second surface of the cover plate, and wherein the first metallization layer provides electrical connection to ground or to potential means.

48. The device of claim 37, further comprising a second metallization layer on the interior surface of the separation compartment.

49. The device of claim 37, further comprising a second metallization layer on the interior surface of the channel compartment.

50. The device of claim 37, further comprising a second metallization layer on the interior surface of the make-up flow compartment.

51. The device of claim 42, wherein the first metallization layer is contiguous and surrounds the MS nozzle, and wherein the first metallization layer provides electrical connection to ground or to potential means.

52. The device of claim 51, further comprising a second metallization layer on the interior surface of the separation compartment.

53. The device of claim 51, further comprising a second metallization layer on the interior surface of the channel compartment.

54. The device of claim 51, further comprising a second metallization layer on the interior surface of the make-up flow compartment.

* * * * *